United States Patent
Sohn et al.

(10) Patent No.: US 9,260,749 B2
(45) Date of Patent: Feb. 16, 2016

(54) GENOME WALKING METHOD FOR CLONING OF UNKNOWN DNA SEQUENCES ADJACENT TO KNOWN SEQUENCES

(75) Inventors: Jung Hoon Sohn, Cheongwon-gun (KR); Jung Hoon Bae, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 363 days.

(21) Appl. No.: 13/345,616

(22) Filed: Jan. 6, 2012

(65) Prior Publication Data

US 2012/0171727 A1 Jul. 5, 2012

Related U.S. Application Data

(63) Continuation-in-part of application No. PCT/KR2010/004365, filed on Jul. 6, 2010.

(30) Foreign Application Priority Data

Jul. 7, 2009 (KR) ........................ 10-2009-0061895

(51) Int. Cl.
 *C12Q 1/68* (2006.01)
(52) U.S. Cl.
 CPC ................... *C12Q 1/6855* (2013.01)
(58) Field of Classification Search
 CPC ...... C12Q 1/686; C12Q 1/689; C12Q 1/6853; C12Q 2525/186; C12Q 2525/155; C12Q 2525/117
 See application file for complete search history.

(56) References Cited

U.S. PATENT DOCUMENTS

| | | | |
|---|---|---|---|
| 6,312,913 B1 | 11/2001 | Wang et al. | |
| 6,777,187 B2 | 8/2004 | Makarov et al. | |
| 7,026,117 B2 | 4/2006 | Soderlund et al. | |
| 2007/0172824 A1 | 7/2007 | Chun | |

FOREIGN PATENT DOCUMENTS

WO 00/60121 A1 10/2000

OTHER PUBLICATIONS

Tsuchiya et al. (Analytical Biochemistry, 2009, vol. 388, 158-160).*
Ukai et al. (Journal of Biotechnology, 2002, 97:233-242).*
Rogers et al. (Biotechniques, 2005, 39:31-34).*
Rosenthal et al. (NAR, 1990, 18(10):3095-3096, IDS reference).*
Kilstrup et al. (NAR, 2000, 28(11):e55, IDS Reference).*
Nthangeni et al. (J Microbiol Method, 2005, 61:225-234, IDS reference).*

(Continued)

*Primary Examiner* — Stephanie K Mummert
(74) *Attorney, Agent, or Firm* — Cooley LLP (57) ABSTRACT

A method and a kit for cloning a nucleotide sequence adjacent to a known nucleotide sequence by PCR are disclosed. The method includes 1) preparing a DNA fragment with cohesive ends by cleaving a DNA that contains the known first nucleotide sequence and the second nucleotide sequence adjacent thereto using a restriction enzyme; 2) modifying the 3' end of the DNA fragment with a nucleotide analog to block further elongation of the DNA fragment; 3) linking the cohesive ends of the 3' end-modified DNA fragment with a linker, adapter or cassette having a cohesive end sequence complementary thereto; and 4) performing PCR using a known first nucleotide sequence-specific primer, and a linker, adapter or cassette sequence-specific primer.

3 Claims, 4 Drawing Sheets (56) References Cited

OTHER PUBLICATIONS

Dominguez et al., Gene walking by unpredictably primed PCR, Nucleic Acids Research, Jul. 1, 1994, 3247-3248, 22 (15).
Karlyshev, Single-Primer PCR Procedure for Rapid Identification of Transposon Insertion Sites, BioTechniques, Jun. 2000, 1078-1082, 28(6).
Kilstrup et al., Rapid genome walking: a simplified oligo-cassette mediated polymerase chain reaction using a single genome-specific primer, Nucleic Acids Research, 2000, 1-4, 28(11).
Liu et al., Thermal Asymmetric Interlaced PCR: Automatable Amplification and Sequencing of Insert End Fragments from P1 and YAC Clones for Chromosome Walking, Genomics, 1995, 674-681, 25.
Nthangeni et al., Development of a versatile cassette for directional genome walking using cassette ligation-mediated PCR and its application in the cloning of complete lipolytic genes from *Bacillus* species, Journal of Microbiological Methods, 2005, 225-234, 61.
Parker et al., Targeted gene walking polymerase chain reaction, Nucleic Acids Research, 1991, 3055-3060, 19(11).
Parks et al., A polymerase chain reaction mediated by a single primer: cloning of genomic sequences adjacent to a serotonin receptor protein coding region, Nucleic Acids Research, 1991, 7155-7160, 19(25).

Padegimas et al., Adaptor Ligation-Based Polymerase Chain Reaction-Mediated Walking, Analytical Biochemistry, 1998, 149-153, 260.
Reddy et al., Global Amplification of cDNA from Limiting Amounts of Tissue, Molecular Biotechnology, 2002, 223-230, 22.
Riley et al., A novel, rapid method for the isolation of terminal sequences from yeast artificial chromosome (YAC) clones, Nucleic Acids Research, 1990, 2887-2890, 18(10).
Rosenthal et al., Genomic walking and sequencing by oligo-cassette mediated polymerase chain reaction, Nucleic Acids Research, 1990, 3095-3096, 18(10).
Rosenthal, PCR amplification techniques for chromosome walking, Tibtech, Jan./Feb. 1992, 44-48, 10.
Siebert et al., An improved PCR method for walking in uncloned genomic DNA, Nucleic Acids Research, Feb. 9, 1995, 1087-1088, 23(6).
Tamme et al., Nonspecific, Nested Suppression PCR Method for Isolation of Unknown Flanking DNA, BioTechniques, May 2000, 895-902, 28(5).
Triglia et al., A procedure for in vitro amplification of DNA segments that lie outside the boundaries of known sequences, Nucleic Acids Research, 1988, 8186, 16(16).
Trueba et al., Random Primed Gene Walking PCR: A Simple Procedure to Retrieve Nucleotide Fragments Adjacent to Known DNA Sequences, BioTechniques, Jul. 1996, 20, 21(1).

\* cited by examiner

GENOME WALKING METHOD FOR CLONING OF UNKNOWN DNA SEQUENCES ADJACENT TO KNOWN SEQUENCES

CROSS-REFERENCES TO RELATED APPLICATIONS

This application is a continuation-in-part of International PCT Patent Application No. PCT/KR2010/004365, which was filed on Jul. 6, 2010, which claims priority to Korean Patent Application No. 10-2009-0061895, filed Jul. 7, 2009. These applications are incorporated herein by reference in their entireties.

SEQUENCE LISTING

The Sequence Listing associated with this application is provided in text format in lieu of a paper copy, and is hereby incorporated by reference into the specification. The name of the text file containing the Sequence Listing is HANO_006_01US_ST25.txt. The text file is about 2 KB, was created on Jan. 6, 2012, and is being submitted electronically via EFS-Web.

TECHNICAL FIELD

The present invention relates to a novel method for cloning a nucleotide sequence adjacent to a known nucleotide sequence by PCR. More particularly, the present invention relates to a method for cloning a second nucleotide sequence adjacent to a known first nucleotide sequence, comprising the steps of 1) preparing a DNA fragment with cohesive ends by cleaving a DNA that contains the known first nucleotide sequence and the second nucleotide sequence adjacent thereto using a restriction enzyme; 2) modifying the 3' end of the DNA fragment with a nucleotide analogue to block further elongation of the DNA fragment; 3) linking the cohesive ends of the 3' end-modified DNA fragment with a linker, adapter or cassette having a cohesive end sequence complementary thereto; and 4) performing PCR using a known first nucleotide sequence-specific primer, and a linker, adapter or cassette sequence-specific primer. Further, the present invention relates to a kit for cloning a second nucleotide sequence adjacent to a known first nucleotide sequence.

BACKGROUND ART

Genome walking refers to a methodology used to clone unknown genomic regions adjacent to known sequences ("known region"), and is also called chromosome walking.

Until now, many methods have been developed for genomic walking. The traditional approach consists of the construction and screening of genomic DNA libraries using the known base sequence as a probe. Before the development of Polymerase Chain Reaction (PCR), this method was most widely used, but has disadvantages in that libraries should be constructed and a great deal of manpower and time are required during the screening process.

The most commonly used PCR based genome walking method is Inverse PCR, where genomic DNA fragments are ligated into circles and the primers designed to recognize the known region in a reverse direction are used to perform amplification (Triglia et al., Nucleic Acid Res. 1988, 16, 8186). One of the drawbacks of Inverse PCR is the requirement for suitable restriction enzyme sites that flank the priming region.

Another method is vectorette PCR, where genomic DNA treated with restriction enzymes is ligated to a cassette containing a mismatch region and then PCR is performed (Riley et al., Nucleic Acid Res. 1990, 18, 2887), and various types of linker- or adapter-ligated PCR have been developed (Isegawa et al., Mol. Cell. Probe. 1992, 6, 467; Siebert et al., Nucleic Acid Res. 1995, 23, 1087; Kilstrup and Kristialsen, Nucleic Acid Res. 2000, 28, e55; Nthangeni et al., J. Microbiol. Methods. 2005, 61, 225).

To improve these methods, methods of performing secondary PCR using blocked adapters (Padegimas and Reichert, Anal. Biochem 1998, 260, 149; Reddy et al., Mol. Biotechnol. 2002, 22, 223), biotinylated primers (Rosenthal and Jones, Nucleic Acid Res. 1990, 18, 3095) or nested primers were developed (Rosenthal, Trends. Biotechnol. 1992, 10, 44). In addition, a method of cloning desired regions using random primers without cassette ligation has been developed (Parker et al., Nucleic Acid Res. 1991, 19, 3055; Park et al., Nucleic Acid Res. 1991, 19, 7155; Domingue and Lopez-Larrea, Nucleic Acid Res. 1994, 22, 3247; Liu and Whittier, Genomics, 1995, 25, 674; Trueba and Johnson, Biotechniques, 1996, 21, 20; Tamme et al., Biotechniques, 2000, 28, 895; Karlyshev et al., Biotechniques, 2000, 28, 1078).

As such, many studies have been made to improve the genome walking method, and thus significant progress has been made. However, it is still in need of improvement. The most serious problems of the PCR-based genome walking methods are low amplification efficiency and non-specific amplification. That is, unwanted genes are amplified together, which makes it difficult to distinguish amplification of desired genes. To improve this problem, complicated multi-step methods were developed, including secondary PCR, purification of desired PCR products using biotinylated primers, or improvement of PCR cycle conditions. However, satisfactory performance has not yet been achieved.

DISCLOSURE

Technical Problem

Therefore, the present inventors have developed a method capable of notably improving upon the above problems. A low amplification efficiency is caused by insufficient ligation between the restricted genomic DNA and cassette, and non-specific amplification is attributed to PCR reaction by only cassette primers instead of a combination of the known region-specific primers and cassette primers. Thus, to amplify the desired region only, amplification by only cassette primers should be inhibited, and amplification by a combination of the known region-specific primers and cassette primers should only be performed. By the present inventors, the restricted genomic DNA fragment was treated with nucleotide analogues such as ddNTP, and ligated with a complementary cassette to increase the efficiency of ligation between the genome and cassette and to prevent non-specific amplification, thereby completing the present invention.

Technical Solution

It is an object of the present invention to provide a method for cloning a second nucleotide sequence adjacent to a known first nucleotide sequence, comprising the steps of 1) preparing a DNA fragment with cohesive ends by cleaving a DNA that contains the known first nucleotide sequence and the second nucleotide sequence adjacent thereto using a restriction enzyme; 2) modifying the 3' end of the DNA fragment with a nucleotide analogue to block further elongation of the DNA fragment; 3) linking the cohesive ends of the 3' end-modified DNA fragment with a linker, adapter or cassette having a cohesive end sequence complementary thereto; and 4) performing PCR using a known first nucleotide sequence-specific primer, and a linker, adapter or cassette sequence-specific primer.

It is another object of the present invention to provide a kit for cloning a second nucleotide sequence adjacent to a known first nucleotide sequence, comprising related enzymes such as DNA polymerases, DNA ligase; a linker, adapter or cassette having a cohesive end sequence complementary to that of the DNA fragment; and a primer specific to the linker, adapter or cassette sequence.

Advantageous Effects

As described above, the present method for cloning a nucleotide sequence adjacent to a known nucleotide sequence by PCR minimizes non-specific amplification and maximizes ligation efficiency of the cassette, and thereby cloning the desired regions can be done by a single PCR reaction without additional experiment. Therefore, the method can be very usefully applied to genome walking technology.

DESCRIPTION OF DRAWINGS

FIG. 3 is the result of testing the genome walking method using the known genes, in which Left shows cassette-ligated genes (URA3 and pBluescript II) and Right is a photograph showing the result of agarose gel electrophoresis after PCR, Lane 1: 1 kb DNA ladder Lane 2: Result of PCR using CP (cassette primer) and GSP (gene-specific primer), after treating 0.5 μg of BamHI-treated pBluescript II and 10 ng of URA3 BamHI fragment with ddGTP, and ligating them with 40 pmol of a cassette Lane 3: Result of PCR using CP and GSP, after treating 0.5 μg of BamHI-treated pBluescript II and 1 ng of URA3 BamHI fragment with ddGTP, and ligating them with 40 pmol of a cassette Lane 4: Result of PCR using CP and GSP, after treating 0.5 μg of BamHI-treated pBluescript II and 0.1 ng of URA3 BamHI fragment with ddGTP, and ligating them with 40 pmol of a cassette Lane 5: Result of PCR using CP and GSP, after treating 0.5 μg of BamHI-treated pBluescript II and 0.01 ng of URA3 BamHI fragment with ddGTP, and ligating them with 40 pmol of a cassette Lane 6: Result of PCR using CP and GSP, after treating 0.5 μg of BamHI-treated pBluescript II and 10 ng of URA3 BamHI fragment with dGTP, and ligating them with 40 pmol of a cassette Lane 7: Result of PCR using CP and GSP, after treating 0.5 μg of BamHI-treated pBluescript II and 1 ng of URA3 BamHI fragment with dGTP, and ligating them with 40 pmol of a cassette Lane 8: Result of PCR using CP and GSP, after treating 0.5 μg of BamHI-treated pBluescript II and 0.1 ng of URA3 BamHI fragment with dGTP, and ligating them with 40 pmol of a cassette Lane 9: Result of PCR using CP and GSP, after treating 0.5 μg of BamHI-treated pBluescript II and 0.01 ng of URA3 BamHI fragment with ddGTP, and ligating them with 40 pmol of a cassette Lane 10: 1 kb DNA ladder.

Lane 1: 1 kb DNA ladder.

Lane 2: PCR result of the BglII cassette flanked library using CP primer and CBH1R primer Lane 3: PCR result of the BamHI cassette flanked library using CP primer and CBH1F primer Lane 4: PCR result of the BglII cassette flanked library using CP primer and CBH2R primer Lane 5: PCR result of the BamHI cassette flanked library using CP primer and CBH2F primer Lane 6: 1 kb DNA ladder.

BEST MODE

In one aspect to achieve the above objects, the present invention relates to a kit for cloning a second nucleotide sequence adjacent to a known first nucleotide sequence, comprising a nucleotide analogue for modifying the 3' end of a DNA fragment; a linker, adapter or cassette having a cohesive end sequence complementary to that of the modified DNA fragment; a primer specific to the known first nucleotide sequence; and a primer specific to the linker, adapter or cassette sequence. The kit for cloning a second nucleotide sequence adjacent to a known first nucleotide sequence may comprises a related enzymes such as DNA polymerases, DNA ligase; a linker, adapter or cassette having a cohesive end sequence complementary to that of the DNA fragment; a primer specific to the known first nucleotide sequence; and a primer specific to the linker, adapter or cassette sequence.

Figure 1:
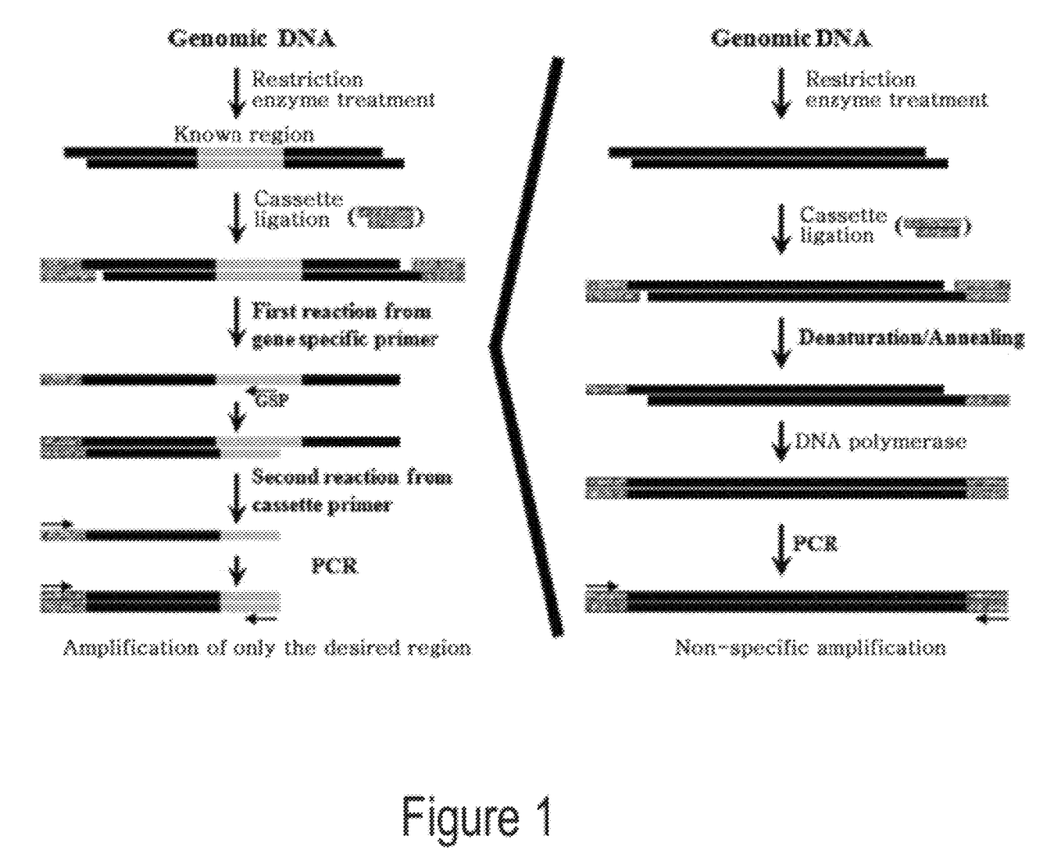
FIG. 1 is a diagram showing a genome walking method using the general cassette-ligation mediated PCR, in which the mark "<" in the drawing represents that the majority of PCR products are occurred by non-specific amplification.

In the known methods of cloning a desired region by ligation of a cassette to the terminal of genomic DNA, it can be expected that the lack of a phosphate group at the 5'-end of the cassette theoretically prevents non-specific amplification, because one strand of the double-stranded cassette is only ligated with the genomic DNA, and thus cassette primers do not bind to the genomic DNA ligated with the single strand cassette, as shown in FIG. 1. That is, first reaction occurs from the known region-specific primer so as to synthesize a new strand, to which a cassette primer binds, and the newly synthesized strand is used as a template to perform PCR, thereby amplifying a desired region.

In the practical use of the method, however, unexpected non-specific amplification frequently occurs. Thus, even though secondary PCR is performed using a nested primer to clone the desired region, it is difficult to obtain the desired region, and many trials and errors are made to amplify the desired region. As shown in the Right of FIG. 1, the genomic DNA ligated with a single strand cassette is denatured, and then it forms double strands, and cassette primer binding site is regenerated to a double-stranded one by DNA polymerase, resulting in non-specific amplification. Since the regenerated double-stranded gene has the double-stranded cassette at both ends thereof, non-specific amplification can be generated by the cassette primer only, irrespective of the known region-specific primer. A target region to be cloned in the genome accounts for only one in several thousands to several ten thousands of the entire genome, and thus non-specific amplification occurs frequently several ten thousand times more than specific amplification. Therefore, it is difficult to detect specific amplification by agarose gel electrophoresis. For successful development of the genome walking method, it is important to prevent non-specific amplification.

Therefore, the present inventors provide a method and a kit capable of minimizing non-specific amplification by modification of the end of a restricted DNA fragment.

As used herein, the term 'nucleotide' refers to a deoxyribonucleotide or ribonucleotide in either single or double-stranded form.

The term "known first nucleotide sequence" refers to a nucleotide sequence of which the base sequence is known, and may include various markers, genes, etc.

The term "second nucleotide sequence adjacent to a known first nucleotide sequence" refers to a nucleotide sequence located within a distance from the known first nucleotide sequence in which it can be amplified by PCR. The second nucleotide sequence may be a genomic region located on the chromosome where the first nucleotide sequence exists. The second nucleotide sequence may contain an unknown gene or a part thereof, and may be a subject of cloning.

Further, the term 'nucleotide analogue' refers to a natural or non-natural occurring analogue being structurally similar to a nucleotide. Herein, the nucleotide analogue is a material that is used not to yield a protruding 3'-OH end by modification at the 3'-end of DNA fragment. Preferably, examples of the nucleotide analogue include, but are not limited to, dideoxynucleotide triphosphate (ddNTP) including ddATP (dideoxyadenosine triphosphate), ddCTP (dideoxycytosine triphosphate), ddGTP (dideoxyguanosine triphosphate), ddTTP (dideoxythymidine triphosphate), ddUTP (dideoxyuridine triphosphate) and ddITP (dideoxyinosine triphosphate). When ddNTP is linked to the end of DNA fragment, further elongation is blocked because ddNTPs lack 3'-OH.

In the known method, as described in FIG. 1, the genomic DNA ligated with a single strand cassette undergoes denaturation/annealing, and then the 3'-OH end thereof is filled by DNA polymerase, thereby producing double-stranded DNA where cassette primers bind. Thus, non-specific amplification occurs frequently. Accordingly, as in the present invention, if the 3'-OH end of DNA fragment is modified with ddNTP for the prevention of further polymerization, non-specific amplification can be remarkably reduced.

As used herein, the term 'cassette' encompasses short double-stranded oligonucleotides that are synthesized to be artificially ligated to the DNA fragment. Because of the lack of a phosphate group at the 5'-end of the cassette, a single strand of double-stranded cassette is only ligated with the DNA fragment.

Similarly, the term 'linker' refers to a short double-stranded DNA synthesized in vitro. Although the linker has blunt ends, but also a restriction enzyme recognition site, both ends thereof can have cohesive ends by treatment of the restriction enzyme even after ligation.

In addition, the term 'adapter' refers to a short double-stranded oligonucleotide, like the linker. However, since the adapter has one blunt end and one cohesive end unlike the linker, it binds to the cohesive end of restricted DNA fragment to form a new DNA molecule having blunt ends.

As used herein, the term 'cassette' may be used instead of 'linker, adapter or cassette'.

As used herein, the term 'DNA construct' refers to a naturally occurring or synthesized nucleic acid construct that contains nucleic acid elements necessary for the expression of structural genes in the host cell. In the present invention, DNA construct refers to a recombinant DNA fragment comprising a DNA fragment that contains a known first nucleotide sequence and a second nucleotide sequence adjacent thereto and that is modified with a nucleotide analogue at the 3' end, and contains a linker, adapter or cassette having a cohesive end sequence complementary to that of the modified DNA fragment.

As used herein, the term 'primer' refers to a short single-stranded nucleic acid sequence having a free 3' hydroxyl group, which is able to undergo base-pairing interaction with a complementary template and serves as a starting point for replicating the template strand. A primer is able to initiate DNA synthesis in the presence of a reagent for polymerization (e.g., DNA polymerase or reverse transcriptase) and four different dNTPs in suitable buffers and at a suitable temperature. A primer specific to the linker, adapter or cassette sequence are included in the kit of the present invention.

The kit of the present invention may further comprise a restriction enzyme, a test tube or other proper container, a reaction buffer solution, deoxynucleotides (dNTP), enzymes such as Taq polymerase, sterilized water or the like for the amplification of genomic DNA fragment.

Figure 2:
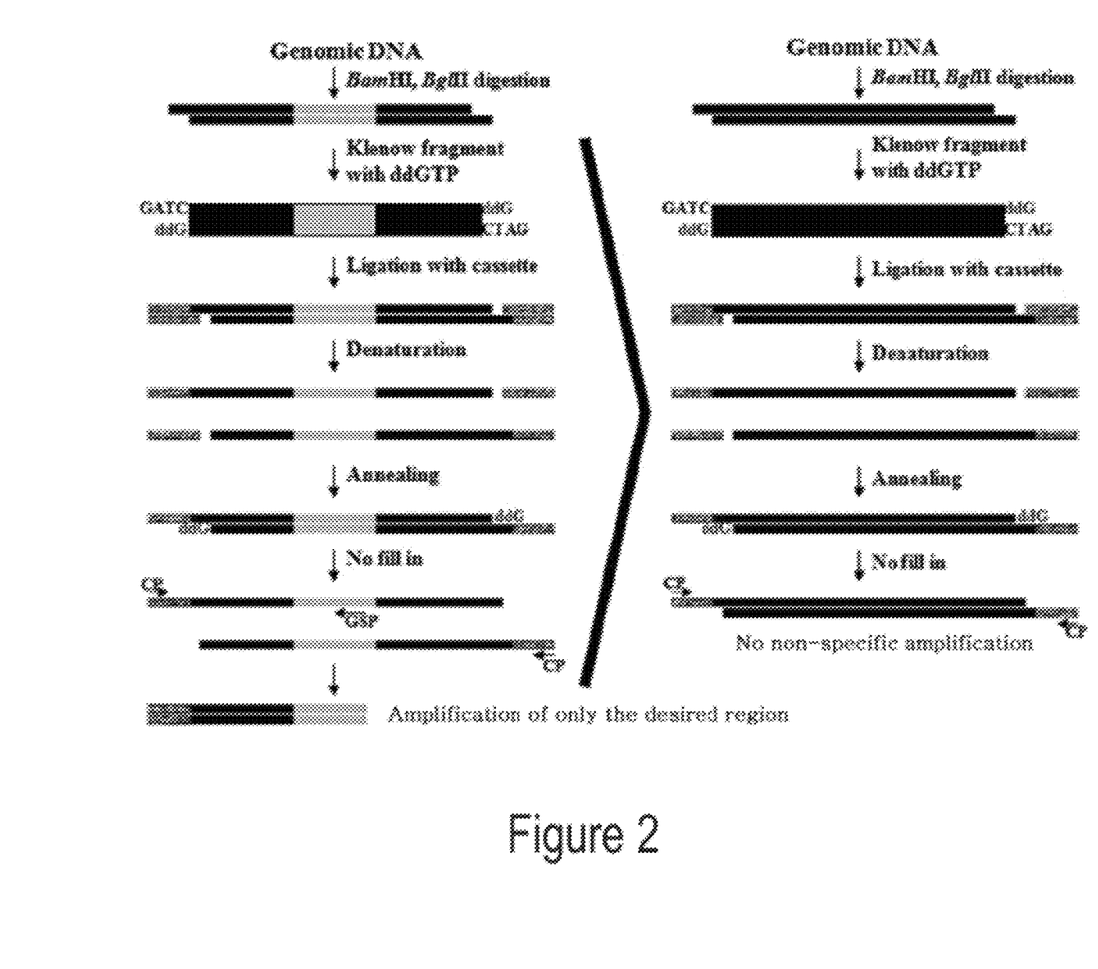
FIG. 2 is a diagram showing a genome walking method improved by non-specific amplification-inhibiting PCR, in which the mark ">" in the drawing represents that the majority of PCR products are occurred by specific amplification.

Using the kit, the present inventors had designed a new genome walking model, where non-specific amplification is inhibited, as shown in FIG. 2.

In still another aspect, the present invention relates to a method for cloning a second nucleotide sequence adjacent to a known first nucleotide sequence, comprising the steps of 1) preparing a DNA fragment with cohesive ends by cleaving a DNA that contains the known first nucleotide sequence and the second nucleotide sequence adjacent thereto using a restriction enzyme;

2) modifying the 3' end of the DNA fragment with a nucleotide analogue to block further elongation of the DNA fragment;

3) linking the cohesive ends of the 3' end-modified DNA fragment with a linker, adapter or cassette having a cohesive end sequence complementary thereto; and 4) performing PCR using a known first nucleotide sequence-specific primer, and a linker, adapter or cassette sequence-specific primer.

Step 1) is a step of cleaving a DNA using a restriction enzyme to prepare a DNA fragment containing a known first nucleotide sequence and a second nucleotide sequence adjacent thereto.

As used herein, the term 'restriction enzymes' an enzyme that recognizes and cleaves a specific base sequence of DNA, and there are restriction enzyme generating blunt ends and restriction enzyme generating cohesive ends. In the present invention, restriction enzyme generating cohesive ends should be used, in order to maximize the efficiency of ligation between the cleaved DNA fragment and cassette.

For example, genomic DNA cleaved by the restriction enzyme, BamHI, BglII or Sau3A has protruding GATC sequences at its 5' end. In addition, the genomic DNA cleaved by Hind has protruding AGTC sequences at its 5' end. The sequences of cohesive ends generated by restriction enzymes are widely known in the art, and thus, this information is used to prepare a DNA fragment having a desired end sequence.

Step 2) is a step of modifying the 3'-OH end of the restricted DNA with a nucleotide analogue. In the present invention, by modification of the 3'-OH end of cleaved DNA fragment with ddNTP for the prevention of further polymerization, non-specific amplification can be remarkably reduced. For example, when the genomic DNA fragment having protruding GATC sequences at its 5' end by treatment with the restriction enzyme BamHI or BglII is reacted with a DNA polymerase Klenow fragment together with dideoxy GTP (ddGTP), ddGTP is inserted into each 3' end of the double-stranded DNA fragment. Further elongation is blocked at each 3' end, because ddGTP lacks 3'-OH needed for DNA polymerization. Consequently, a cassette primer cannot bind thereto, thereby minimizing non-specific amplification.

Step 3) is a step of linking the DNA fragment, which is modified with the nucleotide analogue, with a linker, adapter or cassette having a cohesive end sequence complementary thereto.

In the case where a DNA fragment is treated with a restriction enzyme so as to have cohesive ends, the cohesive ends of cassette are designed to have a sequence complementary to those of the DNA fragment, and they are ligated with each other to give a new DNA construct having cassettes at its both ends. This ligation between the genomic DNA and complementary cassette can improve the efficiency of ligation between the genomic DNA and cassette. For example, when the genomic DNA is cleaved with the restriction enzyme BamHI, BglII or Sau3A, and modified with ddGTP so as to have protruding GAT sequences at each 5' end of double strand, a cassette is designed to have a protruding ATC sequences at its 5' end and one blunt end at the other end, so that it can be ligated with both ends of the modified genomic DNA fragment. Finally, the cassette is able to complementarily bind to the end of genomic DNA. It is also applicable to a linker or adapter.

Further, the efficiency of ligation between the DNA fragment and cassette is more improved by modification of the 3' end of the DNA fragment with ddNTP. That is, if the ends of restricted DNA are partially filled with 1 to 3 bases by DNA polymerase, it can be prevented that the cleaved genes are reconnected to form a circle or multiple binding, because the ends are not complementary to each other. In the same way, the cassette, which is complementary to the ends of a DNA fragment partially filled with bases, cannot be connected to each other. Therefore, the cassette ligation method provided in the present invention minimizes unwanted reaction, and is able to ligate only between the cleaved DNA fragment and cassette at 1:1, thereby maximizing the ligation efficiency.

Step 4) is a step of performing PCR using a known first nucleotide sequence-specific primer, and a linker, adapter or cassette sequence-specific primer to clone the second nucleotide sequence containing an unknown gene.

When the known first nucleotide sequence (known region)-specific primer binds to the known first nucleotide sequence, as in the Left in FIG. 2, a new DNA strand, to which the cassette primer binds, is generated from the known region-specific primer, and therefore, a desired region can be amplified without influence of ddGTP treatment. In addition, without complicated multistep PCR, the desired region can be readily amplified by a single step PCR.

In the present invention, the amplification of nucleotide sequence may be performed by Polymerase Chain Reaction (PCR). PCR is a technique in molecular biology to selectively amplify only a specific DNA fragment in a trace amount of DNA solution, and calls for 30-40 cycles that have three steps of Denaturation, Annealing, and Extension. The type of PCR includes Multiplex-PCR, Nested PCR, Quantitative PCR, real-time PCR, RT-PCR, Touchdown PCR or the like, and any suitable type can be used in the present invention without limitation.

In the specific embodiment of the present invention, prior to application of the method of the present invention to the experiment of cloning a specific region from genomic DNA, a plasmid and a gene, of which base sequence has been known, are used to examine its effect. Specifically, to use yeast URA3 gene as a target for specific amplification, 2.5 kb of BamHI-restriction fragment containing the yeast URA3 gene was used, and to confirm the degree of non-specific amplification, 3 kb of BamHI-restricted pBluescriptII plasmid containing no URA3 gene was used. They were mixed with each other at a proper concentration ratio, and used as PCR template. Under the same conditions, the 3' end of each of them was filled-in with one complementary base using ddGTP or using dGTP as a control group. A cassette having a terminal sequence complementary to that of each fragment is ligated at both ends of the fragment, and then the cassette primer and URA3-specific primer were used to perform PCR.

Figure 3:
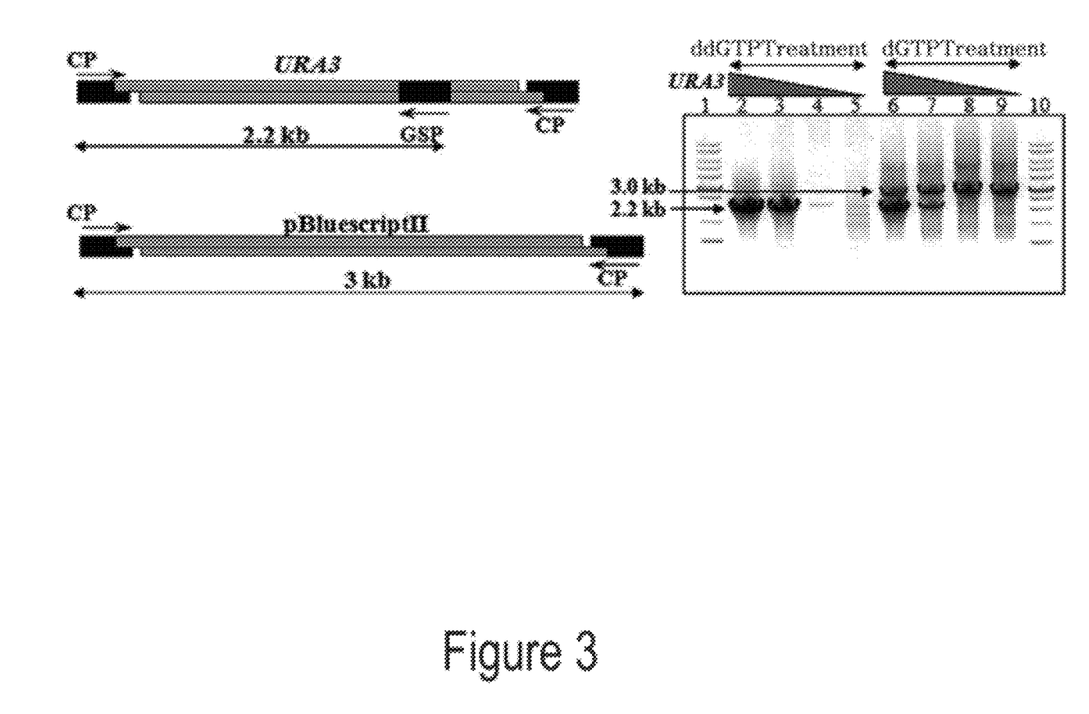

As shown in FIG. 3, in the dGTP-treated sample, it was found that 3 kb of pBluescriptII was amplified (non-specific amplification), irrespective of the concentration ratio of PCR template, and URA3-specific amplification (2.2 kb) occurred at certain concentration ratios. In contrast, in the ddGTP-treated sample, it was found that non-specific amplification did not occur at all concentration ratios, and URA3-specific amplification only occurred.

To practically apply the method of the present invention to the experiment of cloning a specific region from genomic DNA, the fungus *Penicillium* sp. cf4 strain having cellulase activity was identified, and a novel cellulase gene was cloned therefrom. That is, based on the cloned cellulase gene sequence, 11 pairs of degenerate primers were designed to perform PCR of the genomic DNA of the strain. 0.4-kb and 0.45-kb PCR products were obtained, and used as the known regions. Finally, two cellulase genes (PeCBH1 and PeCBH2) containing an unknown sequence adjacent thereto were cloned according to the present invention.

As such, the method of the present invention is advantageous in that it is used to increase the efficiency of ligation between genomic DNA and cassette and inhibit non-specific amplification, thereby readily cloning the desired genomic regions by a single PCR reaction without complicated multi-step PCR, unlike the known genome walking methods.

MODE FOR INVENTION

Hereinafter, the present invention will be described in detail with reference to Examples. However, these Examples are for illustrative purposes only, and the invention is not intended to be limited thereby.

Example 1

Cassette Construction

To examine and confirm the method of the present invention, a double-stranded cassette was first constructed. In order to ligate with genomic DNA which was digested with BamHI, BglII or Sau3A and had one base filled-in with ddGTP, a CSF primer of SEQ ID NO. 1 (GACGCGTAATACGACTCAC-TATAGGGA) and a CSR primer of SEQ ID NO. 2 (ATCTC-CCTATAGTGAGTCGTATTACGCGTC) were synthesized. 40 µl of 100 µM CSF primer and 100 µM CSR primer were mixed with each other, and then 250 mM Tris.Cl (pH 8.0), 10 µl of 100 mM MgCl2 buffer, and 10 µl of distilled water were added, followed by heating in a water bath at 95° C. for 5 min. The water bath was left to cool to room temperature. The cassette constructed by this method had one blunt end and a protruding ATC sequences at its 5'-end.

Example 2

Test on Genome Walking Method Using the Known Genes

Prior to application of the method of the present invention to the experiment of cloning a specific region from genomic DNA, the method was tested using a plasmid and a gene, of which base sequence has been known. As shown in FIG. 3, 2.5 kb of BamHI-restriction fragment containing the URA3 gene and 3 kb of BamHI-restricted pBluescriptII plasmid were used to examine the effect of terminal modification with ddGTP.

0.5 μg of BamHI-restricted pBluescriptII plasmid used as a non-specific DNA and 10 ng, 1 ng, 0.1 ng, and 0.01 ng of URA3 BamHI fragment used as a target gene were mixed, respectively. 1 μl of 2 mM ddGTP and 2 μl of 10× Klenow fragment buffer solution [100 mM Tris.Cl (pH7.5), 70 mM MgCl2, 1 mM DTT] were added, and then distilled water was added to a final volume of 20 μl. Subsequently, 5 units of Klenow fragment (Takara) were added, and reacted at 37° C. for 30 min. For comparison, dGTP was used instead of ddGTP to prepare a control group under the same conditions. DNAs were purified using a PCR purification kit (Axygen, USA) and ligated with 40 pmol of the cassette using a DNA Ligation kit (Takara). The ligation was performed at 16° C. for 30 min, and each DNA was purified using the PCR purification kit (Axygen), and then eluted using 10 μl of distilled water. 1 μl of each eluted sample was used as a template to perform PCR using a cassette primer (CP) of SEQ ID NO. 3 (ACGCGTAATACGACTCACTATAGGGAGATC) and a URA3 gene-specific primer (GSP). The reaction composition was as follows: [1 μl of cassette-ligated DNA, 1 pmol of CP, 1 pmol of GSP, 5 μl of EX taq buffer (Takara), 5 μl of 2.5 mM dNTP, 37 μl of distilled water, and 1 μl of EX taq DNA polymerase(Takara)]. PCR was performed under the conditions of 95° C. 5 min, 30 cycles of 95° C. 30 sec, 60° C. 30 sec, and 72° C. 3 min, and 72° C. 10 min. After reaction was terminated, 10 μl of the reaction solution was analyzed by agarose gel electrophoresis.

As shown in FIG. 3, 3 kb of pBluescriptII was amplified (non-specific amplification) in the dGTP-treated samples (Lanes 6-9), and in contrast, non-specific amplification did not occur in the ddGTP-treated samples (Lanes 2-5). In addition, a 2.2 kb band corresponding to target-specific amplification was detected from 0.01 ng of target gene (1/5000 of pBluescriptII) in the ddGTP-treated samples (Lane 4). Therefore, it can be seen that the method of the present invention minimizes non-specific amplification and maximizes specific amplification, thereby being very useful for genome walking.

Example 3

Cellulase Gene Cloning Using Genome Walking Method

In order to clone a novel cellulase gene, the present inventors selected the fungus having cellulase activity, and identified by sequence analysis a 26 S ribosomal RNA gene, resulting in the identification of a *Penicillium* sp. cf4 strain belonging to the genus *Penicillium*. Based on the cloned cellulase gene sequence, 11 pairs of degenerate primers were designed in order to clone a cellulase gene from the strain. The genomic DNA of the strain was subjected to PCR, and 0.4-kb and 0.45-kb PCR products containing a part of cellulase gene were obtained. Each PCR product was cloned into a pGEM-T Easy vector (Invitrogen), followed by sequence analysis. As a result, both of the PCR products were a part of the exo-glucanase gene, and identical sequences have not been discovered in any genes reported to date. Thus, since there was a high probability that the cellulase gene is a novel gene, a genome cassette library was constructed using other regions of the gene by the method of the present invention, and cloned by the genome walking method.

*Penicillium* sp. cf4 genomic DNA 2 was reacted with 10 units of BamHI and BglII in the presence of 1×BamHI buffer solution (Takara) and 1×BglII buffer solution (Takara) at 37° C. for 2 hrs, and agarose gel electrophoresis was performed to confirm complete cleavage. The reactant was treated with in a 70° C. water bath for 20 min to inactivate the restriction enzymes, and then ddGTP was added to be 0.2 mM, and reacted with 8 units of klenow fragment (Takara) at 37° C. for 30 min. DNA was purified using a PCR purification kit (Axygen), and ligated with 40 pmol of a cassette using a DNA ligation kit (Takara). The ligation was performed at 16° C. for 10 hrs, and then DNA was further purified using the PCR purification kit (Axygen), and eluted using 20 μl of distilled water to construct a BamHI cassette library and a BglII cassette library, respectively.

Figure 4:
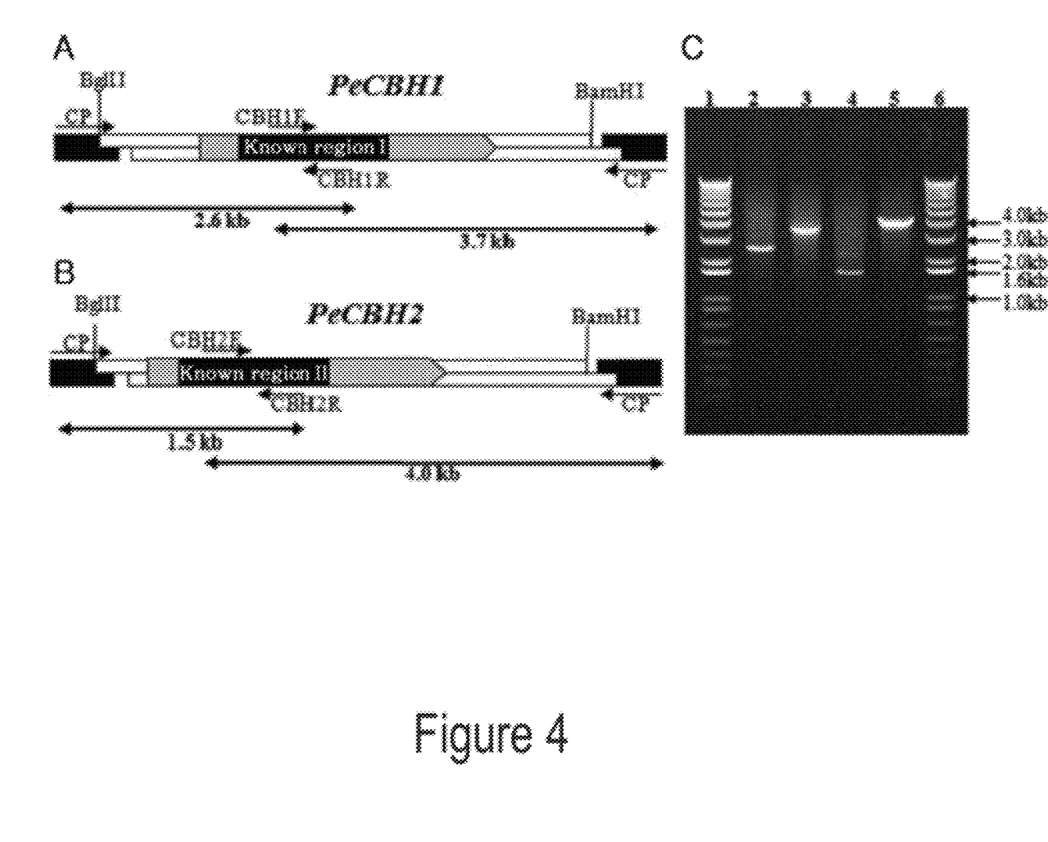
FIG. 4 is a diagram showing the cloning of a novel cellulase gene from the fungal genome using the genome walking method, in which A and B show the structure of a cellulase gene and the position of primers used for cloning cellulase gene, and C is a photograph showing the result of agarose gel electrophoresis after PCR.

To clone the first cellulase gene, as shown in FIG. 4A, 25 bases of cellulase-specific primers (CBH1F, CBH1R) were designed, based on the base sequence of 0.4 kb PCR product (known region I), and PCR was performed using the cassette library 1 μl as a template and the cassette primer CP (SEQ ID NO. 3). The reaction composition for cloning the 5' region of cellulase gene was as follows: [1 μl of genome cassette library, 1 pmol of CP, 1 pmol of CBH1R, 5 μl of EX taq buffer (Takara), 5 μl of 2.5 mM dNTP, 37 μl of distilled water, 1 μl of EX taq DNA polymerase(Takara)]. To clone the 3' region of cellulase gene, the CBH1F primer was used instead of the CBH1R primer. PCR was performed under the conditions of 95° C. 5 min, 30 cycles of 95° C. 30 sec, 60° C. 30 sec, and 72° C. 3 min, and 72° C. 10 min. After reaction was terminated, 10 μl of the reaction solution was analyzed by agarose gel electrophoresis. As a result, a 2.6 kb fragment was amplified from the BglII cassette flanked library in the cloning of 5' region, and a 3.7 kb fragment was amplified from the BamHI cassette flanked library in the cloning of 3' region (FIG. 4C, lanes 2 and 3). Each PCR product was cloned into a pGEM-T Easy vector (Invitrogen), and sequence analysis was performed. As a result, it was confirmed that the desired region was amplified, and the entirety of the sequences of the cellulase gene were identified. The cellulase gene (PeCBH1) derived from *Penicillium* sp. cf4, cloned by the above method, was found to be exo-cellobiohydrolase consisting of 547 amino acids including no intron, 26 secretion signals, and cellulose binding module (CBM) and showed 74.3% similarity to exo-cellobiohydrolase derived from *Penicillium oxalicum*.

To clone the second cellulase gene, as shown in FIG. 4B, 25 bases of cellulase-specific primers (CBH2F, CBH2R) were designed, based on the base sequence of 0.45 kb PCR product (known region II), and PCR was performed in the same manner as above. A 1.5 kb fragment was amplified from the BglII cassette flanked library in the cloning of 5' region, and 4.0 kb fragment was amplified from the BamHI cassette flanked library in the cloning of 3' region (FIG. 4C, lanes 4 and 5). Each PCR product was cloned into a pGEM-T Easy vector (Invitrogen), and sequence analysis was performed. As a result, it was confirmed that the desired region was amplified, and the entire sequences of the second cellulase gene were identified. The second cellulase gene (PeCBH2) derived from *Penicillium* sp. cf4 was found to be exo-cellobiohydrolase consisting of 452 amino acids including two introns and 17 secretion signals, and showed 78.4% similarity to exo-cellobiohydrolase derived from *Penicillium decumbens*.

What is claimed is:

1. A method for cloning a second nucleotide sequence adjacent to a known first nucleotide sequence, consisting of:
   1) preparing a DNA fragment with cohesive ends by cleaving a DNA that contains the known first nucleotide sequence and the second nucleotide sequence adjacent thereto using a restriction enzyme;
   2) modifying the 3' end of the DNA fragment with a dideoxynucleotide triphosphate to block further elongation of the DNA fragment;
   3) linking the cohesive ends of the 3' end-modified DNA fragment with a linker, adapter or cassette having a cohesive end sequence complementary thereto;
   4) performing PCR using a known first nucleotide sequence-specific primer, and a linker, adapter or cassette sequence-specific primer, and thereby amplifying the second nucleotide sequence; and
   5) cloning the second nucleotide sequence.

2. The method according to claim 1, wherein the dideoxynucleotide triphosphate is ddNTP selected from the group consisting of ddATP, ddTTP, ddGTP, ddCTP, ddUTP, and ddITP.

3. A method for cloning a second nucleotide sequence adjacent to a known first nucleotide sequence, comprising:
   1) preparing a DNA fragment with cohesive ends by cleaving a DNA that contains the known first nucleotide sequence and the second nucleotide sequence adjacent thereto using a restriction enzyme;
   2) modifying the 3' end of the DNA fragment with a dideoxynucleotide triphosphate to block further elongation of the DNA fragment, wherein the modification is performed without any prior nucleotide filling-in step;
   3) linking the cohesive ends of the 3' end-modified DNA fragment with a linker, adapter or cassette having a cohesive end sequence complementary thereto;
   4) performing PCR using a known first nucleotide sequence-specific primer, and a linker, adapter or cassette sequence-specific primer, and thereby amplifying the second nucleotide sequence; and
   5) cloning the second nucleotide sequence.

* * * * *

SEQUENCE LISTING

<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: Primer for CSF

<400> SEQUENCE: 1
gacgcgtaat acgactcact ataggga                27

<210> SEQ ID NO 2
<211> LENGTH: 30
<212> TYPE: DNA
<213> ORGANISM: Artificial Sequence
<220> FEATURE:
<223> OTHER INFORMATION: Primer for CSR

<400> SEQUENCE: 2
atctccctat agtgagtcgt attacgcgtc             30

<210> SEQ ID NO 3
<211> LENGTH: 30
<212> TYPE: DNA
<213> ORGANISM: Artificial Sequence
<220> FEATURE:
<223> OTHER INFORMATION: Cassette primer for CP

<400> SEQUENCE: 3
acgcgtaata cgactcacta tagggagatc             30